United States Patent [19]

Cameron et al.

[11] Patent Number: 5,703,108

[45] Date of Patent: Dec. 30, 1997

[54] BONE DEPOSITION BY CERTAIN PROSTAGLANDIN AGONISTS

[75] Inventors: Kimberly O. Cameron, East Lyme, Conn.; Paul A. Dasilva-Jardine, Providence, R.I.; Robert L. Rosati, Stonington, Conn.

[73] Assignee: Pfizer Inc., New York, N.Y.

[21] Appl. No.: 803,307

[22] Filed: Feb. 20, 1997

Related U.S. Application Data

[60] Provisional application No. 60/012,413, Feb. 28, 1996.
[51] Int. Cl.$^6$ ............................................. A61K 31/41
[52] U.S. Cl. .................. 514/382; 514/304; 514/381; 548/252; 548/253
[58] Field of Search ................... 514/304, 381, 514/382

[56] References Cited

U.S. PATENT DOCUMENTS

| | | | |
|---|---|---|---|
| 3,932,389 | 1/1976 | Johnson et al. | 548/252 |
| 4,097,601 | 6/1978 | Schaaf | 514/381 |
| 4,621,100 | 11/1986 | Lund et al. | 514/573 |

*Primary Examiner*—Fiona T. Powers
*Attorney, Agent, or Firm*—Peter C. Richardson; Gregg C. Benson; A. Dean Olson

[57] ABSTRACT

Methods for the treatment of bone disorders utilizing certain prostaglandin agonists/antagonists.

16 Claims, No Drawings

BONE DEPOSITION BY CERTAIN PROSTAGLANDIN AGONISTS

This claims the benefit of provisional application U.S. Ser. No. 60/012,413 filed Feb. 28, 1996, the benefit of which is hereby claimed under 37 C.F.R. §1.78(a)(3).

FIELD OF THE INVENTION

This invention is directed to methods of treating bone diseases using certain prostaglandin agonists. The invention is also directed to preferred prostaglandin agonists and pharmaceutical compositions thereof.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecast to increase three-fold over the next 60 years, and one study estimates that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

There are currently two main types of pharmaceutical therapy for the treatment of osteoporosis. The first is the use of anti-resorptive compounds to reduce the resorption of bone tissue.

Estrogen is an example of an anti-resorptive agent. It is known that estrogen reduces fractures. In addition, Black, et al. in EP 0605193A1 report that estrogen, particularly when taken orally, lowers plasma levels of LDL and raises those of the beneficial high density lipoproteins (HDL's). However, estrogen failed to restore bone to the established osteoporotic skeleton. Furthermore, long-term estrogen therapy, however, has been implicated in a variety of disorders, including an increase in the risk of uterine cancer, endometrial cancer and possibly breast cancer, causing many women to avoid this treatment. The significant undesirable effects associated with estrogen therapy support the need to develop alternative therapies for osteoporosis that have the desirable effect on serum LDL but do not cause undesirable effects.

A second type of pharmaceutical therapy for the treatment of osteoporosis is the use of anabolic agents to promote bone formation and increase bone mass. This class of agents are expected to restore bone to the established osteoporotic skeleton. Commonly assigned U.S. Pat. No. 4,097,601 (the disclosure of which is hereby incorporated by reference) discloses that "while some types of prostaglandins are reported to cause an increase in bone deposition, that effect is not a general phenomenon. U.S. Pat. Nos. 4,000,309, 3,982,016 and 4,018,892 all describe the bone deposition effects resulting from the administration of 16-aryl-13,14-dihydro-PGE$_2$p-biphenyl esters to animals. However, the usual effect exhibited when prostaglandins are administered is not stimulation of bone deposition but bone resorption. The natural prostagalandins, PGE, PGF, PGA and PGB, of the one and two series all are reported to stimulate bone resorption in vitro (J. S. Dietrick, et al. Prostaglandins, 10,231 (1975)). It is, thus, highly unlikely that any particular synthetic prostaglandin will exhibit bone deposition activity.

In view of the bone resorption characteristics of natural prostaglandins and the independent structures of the prostaglandins used in the present invention compared to those used in the U.S. patents supra describing a method of deposition, it has been surprisingly found that 2-descarboxy-2(tetrazol-5-yl)-11-desoxy-16-aryl-ω-tetranor prostaglandins may be used to cause increased bone deposition in animals."

Commonly assigned U.S. Pat. No. 3,932,389 (the disclosure of which is hereby incorporated by reference) discloses certain 2-descarboxy-2-(tetrazol-5-yl)-11 -desoxy-15-substituted-ω-pentanorprostaglandins as being useful for exhibiting diverse physiological effects (e.g., vasodilators, antihypertensives, bronchodilators, antifertility activity, antiulcer activity).

Although there are a variety of osteoporosis therapies there is a continuing need and a continuing search in this field of art for alternative therapies.

SUMMARY OF THE INVENTION

This invention is directed to a method for treating a mammal having a condition which presents with low bone mass comprising administering to a mammal having a condition which presents with low bone mass a therapeutically effective amount of a compound of Formula I

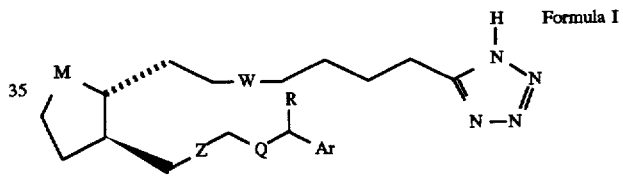

Formula I or a pharmaceutically-acceptable cationic salt thereof wherein

Ar is 3-thienyl, 5(C$_1$–C$_4$alkyl)-2-thienyl, 5(C$_1$–C$_4$alkyl)-3-thienyl, α-napthyl, β-napthyl, tropyl, 3,4-methylenedioxyphenyl;

R is H or methyl;

W is a single bond or a cis double bond;

Z is a single bond or a trans double bond; and

M and Q are each independently carbonyl,

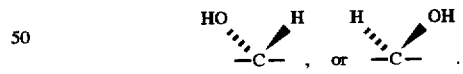

A preferred aspect of this method is the use of preferred compounds of Formula I wherein a. R is H;

M is carbonyl;

W is a single bond;

Z is a single bond;

Q is

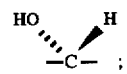

and

Ar is 3,4-methylenedioxyphenyl;

b. R is H;

M is carbonyl;
W is a single bond;
Z is a trans double bond;
Q is

and

Ar is 3,4-methylenedioxyphenyl;
c. R is H;
M is carbonyl;
W is a cis double bond;
Z is a single bond;
Q is

and

Ar is 3,4-methylenedioxyphenyl;
d. R is H;
M is carbonyl;
W is a cis double bond;
Z is a trans double bond;
Q is

and

Ar is 3,4-methylenedioxyphenyl;
e. R is H;
M is carbonyl;
W is a single bond;
Z is a single bond;
Q is

and

Ar is 3,4-methylenedioxyphenyl;
f. R is H;
M is carbonyl;
W is a single bond;
Z is a trans double bond;
Q is

and

Ar is 3,4-methylenedioxyphenyl;
g. R is H;
M is carbonyl;
W is a cis double bond;
Z is a single bond;

Q is

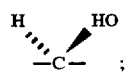

and

Ar is 3,4-methylenedioxyphenyl; and
h. R is H;
M is carbonyl;
W is a cis double bond;
Z is a trans double bond;
Q is

and

Ar is 3,4-methylenedioxyphenyl.

A second preferred aspect of this method is the use of a second group of preferred compounds of Formula I wherein
R is H;
M is carbonyl;
Q is

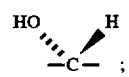

and

Ar is 3-thienyl.

Preferred within this second group is a compound wherein
R is H;
W is a cis double bond;
Z is a trans double bond;
M is carbonyl;
Q is

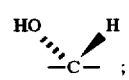

and

Ar is 3-thienyl.

A third preferred aspect of this method is the use of a third group of preferred compounds of Formula I wherein
R is H;
M is carbonyl;
Q is

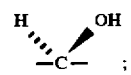

and

Ar is 3-thienyl.

Preferred within this third group is a compound wherein
R is H;
W is a cis double bond;
Z is a trans double bond;
M is carbonyl;

Q is

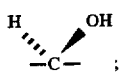

and

Ar is 3-thienyl.

A preferred condition is osteoporosis.

A preferred dosage is about 0.001 to 100 mg/kg/day of the Formula 1 compound. An especially preferred dosage is about 0.01 to 10 mg/kg/day of the Formula I compound.

Yet another aspect of this invention is directed to a compound of Formula II

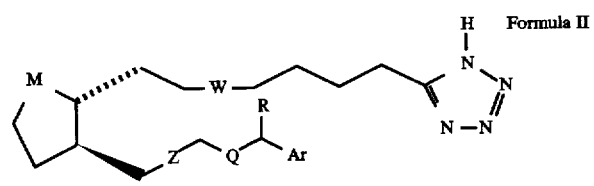

or a pharmaceutically-acceptable salt thereof wherein

Ar is 3-thienyl or 3,4-methylenedioxyphenyl;
R is H or methyl;
W is a single bond or a cis double bond;
Z is a single bond or a trans double bond; and
M and Q are each independently carbonyl,

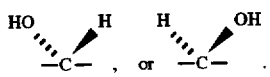

Preferred compounds of Formula II are those compounds wherein
a. R is H;
M is carbonyl;
W is a single bond;
Z is a single bond;
Q is

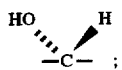

and
Ar is 3,4-methylenedioxyphenyl;
b. R is H;
M is carbonyl;
W is a single bond;
Z is a trans double bond;
Q is

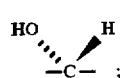

and
Ar is 3,4-methylenedioxyphenyl;
c. R is H;
M is carbonyl;
W is a cis double bond;
Z is a single bond;

Q is

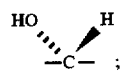

and
Ar is 3,4-methylenedioxyphenyl;
d. R is H;
M is carbonyl;
W is a cis double bond;
Z is a trans double bond;
Q is and
Ar is 3,4-methylenedioxyphenyl;
e. R is H;
M is carbonyl;
W is a single bond;
Z is a single bond;
Q is and
Ar is 3,4-methylenedioxyphenyl;
f. R is H;
M is carbonyl;
W is a single bond;
Z is a trans double bond;
Q is and
Ar is 3,4-methylenedioxyphenyl;
g. R is H;
M is carbonyl;
W is a cis double bond;
Z is a single bond;
Q is and
Ar is 3,4-methylenedioxyphenyl; and
h. R is H;
M is carbonyl;
W is a cis double bond;
Z is a trans double bond;
Q is and
Ar is 3,4-methylenedioxyphenyl.

A second group of preferred compounds of Formula II are compounds wherein

R is H;
M is carbonyl;
Q is

and
Ar is 3-thienyl.
Preferred within this second group is a compound wherein
R is H;
W is a cis double bond;
Z is a trans double bond;
M is carbonyl;
Q is

and
Ar is 3-thienyl.

A third group of preferred compounds of Formula II are compounds wherein
R is H;
M is carbonyl;
Q is

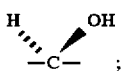

and
Ar is 3-thienyl.
Preferred within this third group is a compound wherein
R is H;
W is a cis double bond;
Z is a trans double bond;
M is carbonyl;
Q is

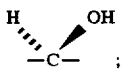

and
Ar is 3-thienyl.

Yet another aspect of this invention is a pharmaceutical composition which comprises a therapeutically effective amount of a compound of Formula II and a pharmaceutically acceptable carrier.

The phrase "condition which presents with low bone mass" refers to a condition where the level of bone mass is below the age specific normal as defined in standards by the World Health Organization "Assessment of Fracture Risk and its Application to Screening for Postmenopausal Osteoporosis (1994). Report of a World Health Organization Study Group. World Health Organization Technical Series 843". Childhood idiopathic and primary osteoporosis are also Included. Included in the treatment of osteoporosis is the prevention or attenuation of long term complications such as curvature of the spine, loss of height, prosthetic surgery, and prevention of prostate malfunctioning. Also included is increasing the bone fracture healing rate and enhancing the rate of successful bone grafts. Also included is periodontal disease or alveolar bone loss.

The phrase "condition which presents with low bone mass" also refers to a mammal known to have a significantly higher than average chance of developing such diseases as are described above including osteoporosis (e.g., postmenopausal women, men over the age of 60, and persons being treated with drugs known to cause osteoporosis as a side effect (such as glucocorticoid)).

Those skilled in the art will recognize that the term bone mass actually refers to bone mass per unit area which is sometimes (although not strictly correctly) referred to as bone mineral density.

The term "treating", "treat" or "treatment" as used herein includes preventative (e.g., prophylactic) and palliative treatment.

The compounds of Formulas I and II are herein defined as the single enantiomer having the absolute stereochemistry depicted in Formulas I and II respectively.

By alkyl is meant straight chain or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

The expression "pharmaceutically-acceptable cationic salt" refers to nontoxic cationic salts Such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included.

The methods and compounds of this invention result in rapid bone formation resulting in decreased fracture rates. This invention makes a significant contribution to the art by providing compounds and methods that increase bone formation resulting in prevention, retardation, and/or regression of osteoporosis and related bone disorders.

Other features and advantages will be apparent from the specification and claims which describe the invention.

DETAILED DESCRIPTION OF THE INVENTION

In general the compounds of this invention can be made by processes which include processes known in the chemical arts, particularly in light of the description contained in U.S. Pat. No. 3,932,389. Some of the preparation methods described therein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, N.Y., 1991. The starting materials and reagents for the above described compounds, are also readily available or can be easily synthesized by those skilled in the art using conventional methods of organic synthesis. For example, many of the compounds used therein, are related to, or are derived from compounds found in nature, in which there is a large scientific interest and commercial need, and accordingly many such compounds are commercially available or are reported in the literature or are easily prepared from other commonly available substances by methods which are reported in the literature. Such compounds include, for example, prostaglandins.

Some of the compounds of this invention have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization.. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

Some of the compounds of this invention are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non- solvent followed by filtration, by evaporation of the solvent, or, in the case of aqueous solutions, by lyophilization, as appropriate.

In addition, when the compounds of this invention form hydrates or solvates they are also within the scope of the invention.

The compounds of this invention are all adapted to therapeutic use as agents that stimulate bone formation and increase bone mass in mammals, particularly humans. Since this function is closely related to the development of osteoporosis and bone related disorders, these compounds, by virtue of their action on bone, prevent, arrest and/or regress osteoporosis.

The utility of the compounds of the present invention as medical agents in the treatment of conditions which present with low bone mass (e.g., osteoporosis) in mammals (e.g. humans, particularly the female) is demonstrated by the activity of the compounds of this invention in conventional assays, including a prostaglandin receptor binding assay (e: g., An. S. et al., Cloning and Expression of the $EP_2$ Subtype of Human Receptors for Prostaglandin $E_2$, Biochemical and Biophysical Research Communication. 1993, 197(1):263–270; Journal of Biological Chemistry, 269 No. 16, pp. 11873–11877, 1994; and the in vivo assay described below (ANABOLIC AGENT PROTOCOL). Such assays also provide a means whereby the activities of the compounds of this invention can be compared to each other and with the activities of other known compounds. The results of these comparisons are useful for determining dosage levels in mammals, including humans, for fie treatment of such diseases.

ANABOLIC AGENT PROTOCOL

The activity of anabolic bone agents In stimulating bone formation and increasing bone mass can be tested in intact male or female rats, sex hormone deficient male (orchidectomy) or female (ovadectomy) rats.

Male or female rats at different ages (such as 3 months of age) are used in the study. The rats are either intact or castrated (ovariectomized or orchidectomized), and subcutaneously injected or orally treated with the anabolic agents to be tested at different doses (such as 1, 3, or 6 mg/kg/day) for certain periods (such as 2 weeks to 2 months). In the castrated rats, treatment is started at the next day after surgery (for the purpose of preventing bone loss) or at the time bone loss has already occurred (for the purpose of restoring bone mass). During the study, all rats are allowed free access to water and a pelleted commercial diet (Teklad Rodent Diet #8064, Harlan Teklad, Madison, Wis.) containing 1.46% calcium, 0.99% phosphorus and 4.96 IU/g of Vit. $D_3$. All rats are given subcutaneous injections of 10 mg/kg calcein on days 12 and 2 before sacrifice.

The rats are sacrificed. The following endpoints are determined;

Femoral Bone Mineral Measurements

The right femur from each rat is removed at autopsy and scanned using dual energy x-ray absorptiometry (DEXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan. speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined Proximal Tibial Metaphyseal Cancellous Bone Histomorphometric Analyses The right tibia is removed at autopsy, dissected free of muscle, and cut into three parts. The proximal tibia is fixed in 70% ethanol, dehydrated in graded concentrations of ethanol, defatted in acetone, then embedded in methyl methacrylate (Eastman Organic Chemicals, Rochester, N.Y.). Frontal sections of proximal tibial metaphyses at 4 and 10 µm thickness are cut using Reichert-Jung Polycut S microtome. One 4 µm and one 10 µm sections from each rat are used for cancellous bone histomorphometry. The 4 µm sections are stained with modified Masson's Trichrome stain while the 10 µm sections remained unstained.

A Bioquant OS/2 histomorphometry system (R&M biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region are omitted in order to restrict measurements to the secondary spongiosa. The 4 µm sections are used to determine indices related to bone volume, bone structure, and bone resorption, while the 10 µm sections are used to determine indices related to bone formation and bone turnover.

I. Measurements and calculations related to trabecular bone volume and structure 1. Total metaphyseal area (TV, $mm^2$): metaphyseal area between 1.2 and 3.6 mm distal to the growth plate-epiphyseal junction.

2. Trabecular bone area (BV, $mm^2$): total area of trabeculae within TV.

3. Trabecular-bone perimeter (BS, mm): the length of total perimeter of trabeculae.

4. Trabecular bone volume (BV/TV, %): BV/TV×100.

5. Trabecular bone number (TBN, #/mm): 1.199/2×BS/TV.

6. Trabecular bone thickness (TBT, μm): (2000/1.199)×(BV/BS).

7. Trabecular bone separation (TBS, μm): (2000×1.199)×(TV-BV).

II. Measurements and calculations related to bone resorption

1. Osteoclast number (OCN, #): total number of osteoclast within total metaphyseal area.

2. Osteoclast perimeter (OCP, mm): length of trabecular perimeter covered by osteoclast.

3. Osteoclast number/mm (OCN/mm, #/mm): OCN/BS

4. Percent osteoclast perimeter (% OCP, %): OCP/BS×100.

III. Measurements and calculations related to bone formation and turnover

1. Single-calcein labeled perimeter (SLS, mm): total length of trabecular perimeter labeled with one calcein label.

2. Double-calcein labeled perimeter (DLS, mm): total length of trabecular perimeter labeled with two calcein labels.

3. Inter-labeled width (ILW, μm): average distance between two calcein labels.

4. Percent mineralizing perimeter (PMS, %): (SLS/2+DLS)/BS×100.

5. Mineral apposition rate (MAR, μm/day): ILW/label interval.

6. Bone formation rate/surface ref. (BFR/BS, $\mu m^2 d/\mu m$):(SLS/2+DLS)×MAR/BS.

7. Bone turnover rate (BTR, %/y): (SLS/2+DLS)×MAR/BV×100.

Statistics

Statistics are calculated using StatView 4.0 packages (Abacus Concepts, Inc., Berkeley, Calif.). The analysis of variance (ANOVA) test followed by Fisher's PLSD is used to compare the differences between groups.

Administration of the compounds of this invention can be via any method which delivers a compound of this invention systemically and/or locally. These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug.

In any event the amount and timing of compounds administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the activity (e.g., bone mass augmentation) that the physician considers appropriate for the patient. In considering the degree of activity desired, the physician must balance a variety of factors such as bone mass starting level, age of the patient, presence of preexisting disease, as well as presence of other diseases (e.g., cardiovascular).

In general an amount of a compound of this invention is used that is sufficient to augment bone mass to a level which is above the bone fracture threshold (as detailed in the World Health Organization Study previously cited herein).

In general an effective dosage for the anabolic agents described above is in the range of 0.001 to 1 00 mg/kg/day, preferably 0.01 to 50 mg/kg/day.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate am employed along with various disintegrants such as starch and preferably potato or tapioca starch and certain complex silicates, together with binding agents such as polyvinyipyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active Ingredient are known, or will be apparent in light of this disclosure, to those skilled in this art. For examples, see *Remington's Pharmaceutical Sciences*, Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated, i.e., a bone disorder.

EXAMPLE 1

Step A 1,3-Benzodioxol-5-yl-acetic acid methyl ester

A solution of 3,4-(methylenedioxy)phenylacetic acid (28.0 g, 155 mmol), catalytic TsOH, and MeOH (125 mL) was stirred over 60 h. Saturated aqueous $NaHCO_3$ was added and the product was extracted into $CH_2Cl_2$. The organic solution was dried ($MgSO_4$), filtered, and concentrated. Distillation (120 –1° C., 1 mmHg) provided the title compound as a clear and colorless oil (27.6 g). $^1H$ NMR (250 MHz, $CDCl_3$): δ6.74 (m, 3H), 5.94 (s, 2H), 3.69 (s, 3H), 3.54 (s, 2H).

Step B

[3-(1,3-Benzodioxol-5-yl)-2-oxo-propyl]-phosphonic acid dimethyl ester n-BuLi (2.5M in hexanes, 125 mL, 312 mmol) was added slowly to a solution of dimethyl methyl phosphonate (36.4 g, 293 mmol) in THF (300 mL) at −78° C. After the addition was complete, the mixture was stirred for an additional 10 minutes and 1,3-benzodioxol-5-yl-acetic acid methyl ester (27.63 g, 142.3 mmol) was added all at once. The reaction was stirred for 40 minutes, AcOH (200 mL) was added, and the reaction was brought to room temperature. The volatiles were removed in vacuo. Water and EtOAc were added and the product was extracted into EtOAc. The combined organic layers were washed with brine, dried ($MgSO_4$), filtered, and concentrated. Unreacted starting materials were removed via distillation to yield product as a viscous oil (28.087 g). $^1$H NMR (250 MHz, $CDCl_3$): δ6.69 (m,3H), 5.92 (s,2H), 3.77 (s,2H), 3.76 (d, J=11.3 Hz, 6H), 3.08 (d, J=22.6 Hz, 2H).

Step C

[3aR[3aα,4α(E),6aα]]-4-[4-(1,3-Benzodioxol-5-yl)-3-oxo-1-butenyl] hexahydro-2H-cyclopenta[b]furan-2-one.

A solution of [3-(1,3-benzodioxol-5-yl)-2-oxo-propyl]-phosphonic acid dimethyl ester (6.69 g, 23.4 mmol) in THF (50 mL) was added slowly to a mixture of NaH (60% in oil, 856 mg, 21.4 mmol) in THF (200 mL). After the addition was complete, the reaction was stirred for 1 h, and [3aR-(3aα,4α,6aα)]-hexahydro-2-oxo-2 H-cyclopenta[b]furan-4-carboxaldehyde (3.0 g, 19.5 mmol) in THF (50 mL) was added dropwise. The reaction was stirred for 0.5 h and $H_2O$ and EtOAc were added. The layers were separated and the aqueous layer was extracted with EtOAc. The combined organic layers were washed with water, saturated aqueous $NaHCO_3$ and brine. The organic solution was dried ($MgSO_4$), filtered, and concentrated to an amber oil. Flash chromatography (solvent gradient: hexanes to 60:40 hexanes:EtOAc) provided the title compound (4.35 g).

Step D

[3aR[3aα,4α(E),6aα]]-4-[4-(1,3-Benzodioxol-5-yl)-3-hydroxy-1-butenyl]hexahydro-2H-cyclopenta[b]furan-2-one A mixture of [3aR-[3aα,4α(E),6aα]]-4-[4-(1,3-benzodioxol-5-yl)-3-oxo-1-butenyl]hexahydro-2H-cyclopenta[b]furan-2-one. (4.35 g, 13.8 mmol), $CeCl_3$ ($H_2O)_7$ (2.06 g, 5.50 mmol), and MeOH were cooled to −78° C. and $NaBH_4$ (784 mg, 20.7 mmol) was added. The mixture was allowed to warm to room temperature and was stirred for 1 h. The reaction was poured into $H_2O$ and the product was extracted into EtOAc. The aqueous layer was acidified (pH=6) with 1N HCl and was further extracted with EtOAc. The EtOAc layers were combined and were washed with water followed by brine. The organic. solution was dried ($MgSO_4$), filtered, and concentrated. Flash chromatography provided the desired product (2.35 g). $^1$H NMR (400 MHz, $CDCl_3$): δ 6.68 (m,3H), 5.92 (s,2H), 5.52(m,2H), 4.93 (m,1H), 4.24 (m,1H), 2.70 (m,3H), 2.41 (m, 1H), 2.33 (m,2H), 2.22 (m,1H), 1.92 (m,2H), 1.46 (m,1H).

Step E

[3aR-[3aα,4α(E),6aα]]-4-[4-(1,3-Benzodioxol-5-yl)-3-[[(1,1-dimethylethyl)dimethylsilyl]oxy]-1-butenyl] hexahydro-2H-cyclopenta[b]furan-2-one A solution of [3aR-[3aα,4α(E),6aα]]-4-[4-(1,3-benzodioxol-5-yl)-3-hydroxy-1-butenyl]hexahydro-2H-cyclopenta[b]furan-2-one (2.05 g, 6.48 mmol), dimethyl-tert-butylsilylchloride (1.22 g, 8.09 mmol), imidazole (1.1 g, 16.2 mmol), and DMF were heated to 35° C. overnight. The reaction was poured into $H_2O$ and the product was extracted into EtOAc. The combined organic layers were washed with $H_2O$ and brine and were dried ($MgSO_4$), filtered, and concentrated to a colorless oil (2.76 g) that was used without further purification.

Step F

[3aR-[3aα,4α(E),6aα]]-4-[4-(1,3-Benzodioxol-5-yl-3-[[(1,1-dimethylethyl)dimethylsilyl]oxy]-1-butenyl] hexahydro-2H-cyclopenta[b]furan-2-ol Diisobutylaluminum hydride (1.0M in hexanes, 6.2 mL) was added dropwise to a solution of [3aR-[3aα,4α(E),6aα]]-4-[4-(1,3-benzodioxol-5-yl)-3-[[(1,1-dimethylethyl)dimethylsilyl]oxy]-1-butenyl]-hexahydro-2H-cyclopenta[b]furan-2-one. (2.70 g, 6.27 mmol) in $CH_2Cl_2$ (100 mL) at −78° C. After 1 h, additional diisobutylaluminum hydride (6.2 mL) was added and the reaction was stirred for 0.5 h. MeOH (5 mL) was added followed by $H_2O$ (5 eq) and NaF (20 eq). The mixture .was warmed to room temperature and was diluted with $Et_2O$. The reaction was filtered through celite and the filtrate was concentrated in vacuo to provide the title compound (2.64 g) which was used without further purification.

Step G

[1S-[1α,2α(Z),3α(E)]]-3-[4-(1,3-Benzodioxol-5-yl)-3-[[(1,1-dimethylethyl)dimethylsilyl]oxy]-1-butenyl]-2-[6-(1H-tetrazol-5-yl)-2-hexenyl]-cyclopentanol Potassium bis(trimethylsilyl)amide (0.5M in toluene, 73.2 mL) was slowly added to a solution of [4-(tetrazol-5-yl)-butyl]triphenylphosphonium bromide (8.55 g, 18.3 mmol) in THF. The bright orange solution was stirred for 0.5 h and a solution of [3aR-[3aα,4 α(E),6aα]]-4-[4-(1,3-benzodioxol-5-yl)-3-[[(1,1-dimethylethyl) dimethylsilyl] oxy]-1-butenyl]hexahydro-2H-cyclopenta[b]furan-2-ol (2.64 g, 6.10 mmol) in THF was slowly added. After stirring for 1 h, $H_2O$ and $Et_2O$ were added. The aqueous layer was extracted with $Et_2O$ and was acidified to pH=7.0 with 1N HCl and was extracted with $Et_2O$. The ethereal layers were dried ($MgSO_4$), filtered, and concentrated to provide the title compound (1.35 g). $^1$H NMR (400 MHz, $CDCl_3$): δ 6.63 (m,3H), 5.88 (2, 2H), 5.36 (m,4H), 4.32 (m,1H), 4.17 (m,1H).

Step H

[2R-[2α(Z),3β(E)]]-3-[4-(1,3-Benzodioxol-5-yl)-3-[[(1,1-dimethylethyl)dimethylsilyl]oxy]-1-butenyl]-2-[6-(1H-tetrazol-5-yl)-2 -hexenyl]-cyclopentanone A mixture of [1S-[1α,2α(Z),3β(E)]]-3-[4-(1,3-benzodioxol-5-yl)-3-[[(1,1-dimethylethyl)dimethylsilyl]oxy]-1-butenyl]-2-[6-(1H-tetrazol-5-yl)-2-hexenyl]-cyclopentanol (1.30 g, 2.4 mmol), Dess-Martin periodinane (1.12 g, 2.6 mmol), and $CH_2Cl_2$ was stirred at room temperature for 20 h. Additional periodinane (500 mg) was added and the reaction was stirred at room temperature until starting material-was consumed. The reaction was washed with saturated aqueous sodium thiosulfate and the organic solution was washed consecutively with 1N HCl, aqueous saturated $NaHCO_3$ solution, $H_2O$, and brine. The organic- solution was dried ($MgSO_4$), filtered, and concentrated to yield 740 mg of the title compound.

Step I

[2R-(2α,3β)]-3-[4-(1,3-Benzodioxol-5-yl)-3-hydroxyl-1-butenyl]-2-[6-(1H-tetrazol-5-yl)-2-hexanyl]-cyclopentanone Tetrabutylammonium fluoride (1M in THF, 10 mL) was added to a solution of [2R-[2α(Z),3β(E)]]-3-[4-(1,3-benzodioxol-5-yl)-3-[[(1,1-dimethylethyl)dimethylsilyl]oxy]-1-butenyl]-2-[6-(1H-tetrazol-5-yl)-2-hexenyl]-cyclopentanone (640 mg, 1.18 mmol) in THF (40 mL). The reaction was stirred for 3 h and was poured into $H_2O$. The aqueous layer was extracted with $Et_2O$. The combined organic layers were washed with $H_2O$ and brine and was dried ($MgSO_4$), filtered, and concentrated. Radial chromatography (solvent gradient: $CH_2Cl_2$ (9:1 $CH_2Cl_2$:MeOH) provided the title compound (210 mg). $^1$H NMR (400 MHz, $CDCl_3$): $\delta^1$H NMR (250 MHz, $CDCl_3$): δ 6.67 (m,3H), 5.87 s,2H), 5.64 (m,4H), 5.27 (m,2H), 4.36 (m,1H), 2.93 (m,2H), 2.79 (m,2H).

Step J

[2R-(2α,3β)]-3-[4-(1,3-Benzodioxol-5-yl)-3-hydroxybutyl]-2-[6-(1H-tetrazol-5-yl)hexyl]-cyclopentanone To a solution of [2R-(2α,3β)]-3-[4-(1,3-benzodioxol-5-yl)-3-hydroxyl-1-butenyl]-2-[6-(1H-tetrazol-5-yl)-2-hexenyl]-cyclopentanone (105 mg, 0.247 mmol) in EtOAo (25 mL) was added 10% Pd on carbon (105 mg). The solution was hydrogenated at 50 psi for 20 h. The solids were removed via filtration through celite and the volatiles were removed in vacuo. Radial chromatography (solvent gradient: $CH_2Cl_2$ to (9:1 $CH_2Cl_{21}$:MeOH, then EtOAc-:MeOH 95:5) provided the title compound (21 mg). $^1$H NMR (400 MHz, $CDCl_3$): δ 6.68 (m,3H), 5.90 (s,2H), 3.80 (m,1H), 2.95 (m,2H).

Step K

Potassium salt of [2R-(2α,3β)]-3-[4-(1,3-Benzodioxol-5-yl)-3-hydroxybutyl]-2-[6-(1H-tetrazol-5-yl)hexyl]-cyclopentanone

[2R-(2α,3β)]-3-[4-(1,3-Benzodioxol-5-yl)-3-hydroxybutyl]-2-[6-(1H-tetrazol-5-yl)hexyl]-cyclopentanone (95.3 mg, 0.224 mmol) was dissolved in absolute EtOH and $K_2CO_3$ (31 mg, 0.224 mmol) in 1 mL $H_2O$ was added. The reaction was stirred for 1 h and was concentrated in vacuo to provide the potassium salt.

EXAMPLE 2

Synthesis of [2R-[2α(Z),3β(E)]]-2-[6-(1H-tetrazol-5yl)-2-hexenyl]-3-[4-(thienyl-3-yl)-3-hydroxyl-1-butenyl]-cyclopentanone

Step A 3-(Thienyl-3-yl)-2-oxo-propyl)-phosphonic and dimethyl ester

Using the procedure of Example 1, Step B, 10 g of commercially available 3-thienyl acetic acid methyl ester was converted to 5 g of the titled substance $^1$HNMR(CDCl$_3$) 3.94(2H,S).

Step B

3aR-[3aα,4α(E),6aα]]-4-[4-(Thienyl-3-yl)-3-oxo-1-butenyl]hexahydro-2H-Cyclopenta[b]furan-2-one Using the procedure of Example 1, Step C, 2.41 g of the previously synthesized phosphoric acid dimethyl ester was converted into 1.25 g of the titled substance. MS:277 ($P^+$+1).

Step C

[3aR-[3aα,4α(E),6aα]]-4-[4-(Thienyl-3-yl)-3-hydroxy-1-butenyl]hexahydro-2H-Cyclopenta[b]furan-2-one Using the procedure of Example 1, Step D, 1.21 g of the previously synthesized ketone was conveded to 1.37 g of the titled substance. MS296($P^+$+1).

Step D

[3aR-[3aα,4α(E),6aα]]-4-[4-(Thienyl-3-yl)-3-[[1,1-Dimethylethyl) dimethylsilyl]oxy]-1-butenyl]hexahydro-2H-Cyclopenta[b]furan-2-one Using the procedure of Example 1, Step E, 1.37 g of the previously synthesized alcohol was converted to 1.80 g of the title substance. MS 393 ($P^+$+1).

Step E

[3aR-[3aα,4α(E),6aα]]-4-[4-(thienyl-3-yl)-3[(1,1-dimethylethyl) dimethylsilyl]oxy]-1-butenyl]hexahydro-2H-cyclopenta[b]furan-2-ol Using the procedure of Example 1, Step F, 1.80 g of the previously synthesized silyl lactone was converted into 1.72 g of the titled substance. MS 395 ($P^+$+1).

Step F

[1S-[1α,2α(Z),3β(E)]]-3-[4-thienyl-3-yl)-2-[[(1,1-dimethylethyl) dimethylsilyl]oxy]-1-butenyl]-2-[6-(1H-tetrazol-5-yl)-2-hexenyl]-cyclopentanol Using the procedure Example 1, Step G, 1.68 g of the previously synthesized silyl lactol was converted into 0.625 g of the titled substance. MS ($P^+$−1) 501.

Step G

[2R-[2α(Z),3β,(E)]]-2-[6-(1H-tetrazol-5-yl)-2-hexenyl]-3-[4-(thienyl-3-yl)-3-[[(1,1-dimethylethyl)dimethylsilyl]oxy]-1-butenyl]-cyclopentananone Using the procedure of Example 1, Step H, 0.613 g of the previously synthesized cyclopentanol was converted into 0.683 g of the titled substance. MS 499 ($P^+$−1).

Step H

[2R-[2α(Z),3β(E)]]-2-[6-(1H-tetrazol-5-yl)-2-hexenyl]-3-[4-(thienyl-3-yl)-3-hydroxyl-1-butenyl]-cyclopentanone Using the procedure of Example 1, Step 1, 0.683 g of the previously synthesized silyloxyl cyclopentanone was converted into 0.183 g of the titled substance. MS ($P^+$−1) 384.

It should be understood that the invention is not limited to the particular embodiments described herein, but that various changes and modifications may be made without departing from the spirit and scope of this novel concept as defined by the following claims.

We claim:

1. A method for treating a mammal having a condition which presents with low bone mass comprising administering to a mammal having a condition which presents with low bone mass a therapeutically effective amount of a compound of Formula I

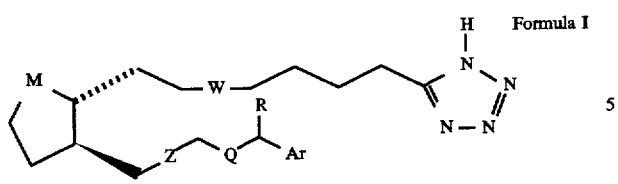

Formula I or a pharmaceutically-acceptable cationic salt thereof wherein

Ar is 3-thienyl, 5($C_1$–$C_4$alkyl)-2-thienyl, 5($C_1$–$C_4$alkyl)-3-thienyl, α-napthyl, β-napthyl, tropyl, 3,4-methylenedioxyphenyl;

R is H or methyl;

W is a single bond or a cis double bond;

Z is a single bond or a trans double bond; and

M and Q are each independently carbonyl,

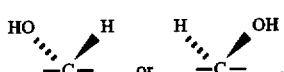
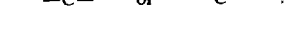

2. A method as recited in claim 1 wherein

R is H;

M is carbonyl;

W is a single bond;

Z is a single bond;

Q is

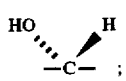

and

Ar is 3,4-methylenedioxyphenyl.

3. A method as recited in claim 1 wherein

R is H;

M is carbonyl;

W is a single bond;

Z is s trans double bond;

Q is

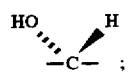

and

Ar is 3,4-methylenedioxyphenyl.

4. A method as recited in claim 1 wherein

R is H;

M is carbonyl;

W is s cis double bond;

Z is a single bond;

Q is

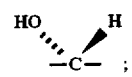

and

Ar is 3,4-methylenedioxyphenyl.

5. A method as recited in claim 1 wherein

R is H;

M is carbonyl;

W is a cis double bond;

Z is a trans double bond;

Q is

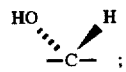

and

Ar is 3,4-methylenedioxyphenyl.

6. A method as recited in claim 1 wherein

R is H;

M is carbonyl;

W is a single bond;

Z is a single bond;

Q is

and

Ar is 3,4-methylenedioxyphenyl.

7. A method as recited in claim 1 wherein

R is H;

M is carbonyl;

W is a single bond;

Z is a trans double bond;

Q is

and

Ar is 3,-methylenedioxyphenyl.

8. A method as recited in claim 1 wherein

R is H;

M is carbonyl;

W is a cis double bond;

Z is a single bond;

Q is

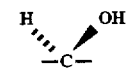

and

Ar is 3,4-methylenedioxyphenyl.

9. A method as recited in claim 1 wherein

R is H;

M is carbonyl;

W is a cis double bond;

Z is a trans double bond;

Q is

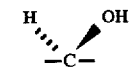

and

Ar is 3,4-methylenedioxyphenyl.

10. A method as recited in claim 1 wherein
R is H;
M is carbonyl;
Q is

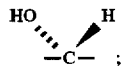

and

Ar is 3-thienyl.
11. A method as recited in claim 1 wherein
R is H;
W is a cis double bond;
Z is a trans double bond;
M is carbonyl;
Q is

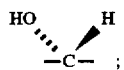

and

Ar is 3-thienyl.
12. A method as recited in claim 1 wherein
R is H;
M is carbonyl;
Q is

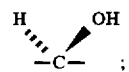

and

Ar is 3-thienyl.
13. A method as recited in claim 1 wherein
R is H;
W is a cis double bond;
Z is a trans double bond;
M is carbonyl;
Q is

and

Ar is 3-thienyl.
14. A method as recited in claim 1 wherein the condition is osteoporosis.
15. A method as recited in claim 1 wherein about 0.001 to 100 mg/kg/day of the Formula I compound is administered.
16. A method as recited in claim 15 wherein about 0.01 to 10 mg/kg/day of the Formula I compound is administered.

* * * * *